US012661029B2

(12) United States Patent
Foo et al.

(10) Patent No.:  US 12,661,029 B2
(45) Date of Patent:       Jun. 23, 2026

(54) MAGNETIC RESONANCE SYSTEMS HAVING ULTRA-WIDE BORES AND PATIENT SUPPORT ASSEMBLIES WITH PRECISE POSITIONING

(71) Applicant: GE PRECISION HEALTHCARE LLC, Wauwatosa, WI (US)

(72) Inventors: Thomas Kwok-Fah Foo, Clifton Park, NY (US); Robert D. Darrow, Glenville, NY (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 379 days.

(21) Appl. No.: 18/158,547

(22) Filed: Jan. 24, 2023

(65) Prior Publication Data

US 2024/0245318 A1      Jul. 25, 2024

(51) Int. Cl.
*A61B 5/055*          (2006.01)
*A61G 13/02*          (2006.01)

(52) U.S. Cl.
CPC .............. *A61B 5/055* (2013.01); *A61G 13/02* (2013.01)

(58) Field of Classification Search
CPC ....... A61B 5/055; A61B 5/704; A61B 6/0407; A61B 6/0487; A61B 6/4447; A61B 90/50; A61B 34/30; A61G 13/02; A61G 13/00; A61G 13/10; A61G 13/04; A61G 13/06; A61G 13/08
See application file for complete search history.

(56) References Cited

U.S. PATENT DOCUMENTS

| | | | | |
|---|---|---|---|---|
| 6,138,302 | A * | 10/2000 | Sashin | A61B 6/0421 |
| | | | | 5/601 |
| 6,322,251 | B1 * | 11/2001 | Ballhaus | A61G 13/00 |
| | | | | 378/208 |
| 8,401,612 | B1 * | 3/2013 | Chu | A61B 5/4058 |
| | | | | 5/607 |
| 9,408,554 | B2 * | 8/2016 | Gregerson | A61B 6/4405 |
| 2003/0079287 | A1 * | 5/2003 | Truwit | A61B 5/704 |
| | | | | 5/601 |
| 2012/0174317 | A1 * | 7/2012 | Saracen | A61B 6/0487 |
| | | | | 901/29 |
| 2014/0098934 | A1 * | 4/2014 | Kondo | A61B 6/0407 |
| | | | | 5/601 |

(Continued)

FOREIGN PATENT DOCUMENTS

CN          109862845  B   * 12/2022  ............. A61B 34/00

OTHER PUBLICATIONS

Blanco RT et al., "Interventional and intraoperative MRI at low field scanner—a review" Eur J Radiol 2005; 56: 130-142.

(Continued)

*Primary Examiner* — Justin C Mikowski
*Assistant Examiner* — George Samuel Gines
(74) *Attorney, Agent, or Firm* — Armstrong Teasdale LLP

(57)          ABSTRACT
A magnetic resonance (MR) system is provided. The MR system includes a magnet assembly defining a bore, wherein the bore has a diameter of 80 centimeter (cm) or greater, and a patient support assembly. The patient support assembly includes a table configured to accommodate a subject and configured to be positioned at least partially in the bore, and a carriage assembly attachable to the table and configured to drive the table to move in at least two degrees-of-freedom.

17 Claims, 8 Drawing Sheets

(56)                    References Cited

U.S. PATENT DOCUMENTS

| | | | |
|---|---|---|---|
| 2016/0000629 A1* | 1/2016 | Jackson | A61G 13/02 |
| | | | 5/601 |
| 2018/0055414 A1* | 3/2018 | Bieri | G01R 33/4816 |
| 2018/0085603 A1* | 3/2018 | Kruesi | A61B 6/04 |
| 2021/0103019 A1* | 4/2021 | Liu | G01R 33/4808 |
| 2022/0378385 A1* | 12/2022 | Campagna | A61B 6/0407 |
| 2022/0378524 A1* | 12/2022 | Schreiber | A61B 6/582 |

OTHER PUBLICATIONS

Gorczyca DP et al., "Silicone breast implant rupture: comparison between three-point Dixon and fast spin-echo MR Imaging", AJR Am J Roentgenol 1994; 162: 305-310.

Hu X et al., The total resection rate of glioma can be improved by the application of US-MRI fusion combined with contrast-enhanced ultrasound, Clin Neurol Neurosurg 2021; 208: 106892.

Malyarenko DI et al., "Retrospective Correction of ADC for Gradient Nonlinearity Errors in Multicenter Breast DWI Trials: ACRIN6698 Multiplatform Feasibility Study", Tomography 2020; 6: 86-92.

Maubon AJ et al., "Effect of field strength on MR images: comparison of the same subject at 0.5, 1.0, and 1.5 T", Radiographics 1999; 19: 1057-1067.

Newitt DC et al., "Gradient nonlinearity correction to improve apparent diffusion coefficient accuracy and standardization in the american college of radiology imaging network 6698 breast cancer trial", J Magn Reson Imaging 2015; 42: 908-919.

Nitsch J et al., "Automatic and efficient MRI-US segmentations for improving intraoperative image fusion in image-guided neurosurgery", Neuroimage Clin 2019; 22: 101766.

Noh T et al., "Intraoperative Imaging for High-Grade Glioma Surgery", Neurosurg Clin N Am 2021; 32: 47-54.

Schenck JF et al., "Superconducting open-configuration MR imaging system for image-guided therapy", Radiology 1995; 195: 805-814.

Shellock FG et al., "Kinematic MR imaging of the patellofemoral joint: comparison of passive positioning and active movement techniques", Radiology 1992; 184: 574-577.

Shellock FG et al., "Patellofemoral joint: identification of abnormalities with active-movement, "unloaded" versus "loaded" kinematic MR imaging techniques", Radiology 1993; 188: 575-578.

Tan ET et al., "Improved correction for gradient nonlinearity effects in diffusion-weighted imaging", J Magn Reson Imaging 2013; 38: 448-453.

Wujciak D., "Moderne Mittelfeld-Magnetresonanztomographie in der Niederlassung : Erfahrungsbericht. [Modern mid-field magnetic resonance imaging in private practice : Field report]", Radiologe 2022; 62: 405-409, Abstract Only.

\* cited by examiner

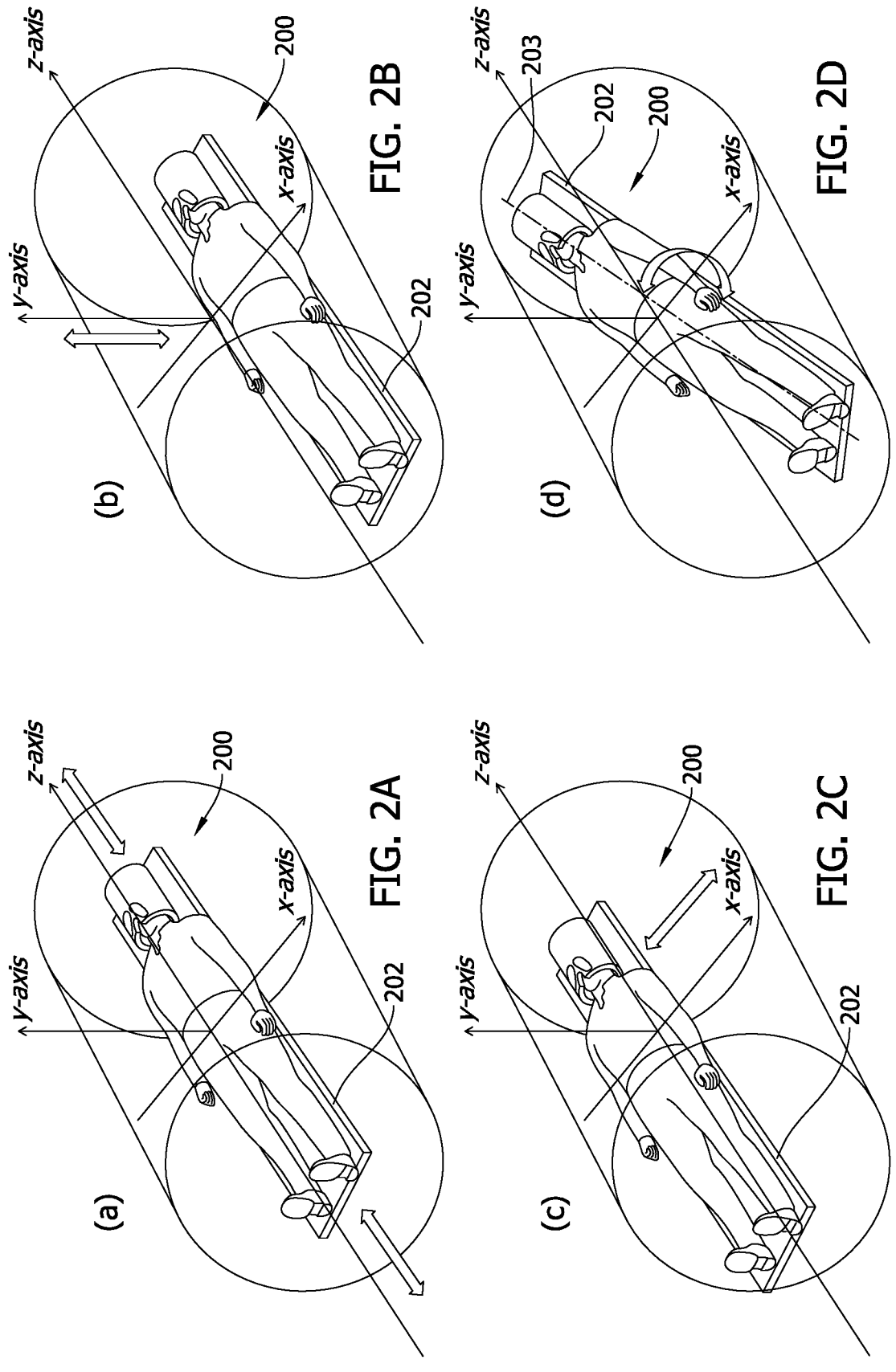

Standard Lithotomy

Low Lithotomy

Hemi (split) Lithotomy

Tilted Low Lithotomy

PRIOR ART 70 cm

MAGNETIC RESONANCE SYSTEMS HAVING ULTRA-WIDE BORES AND PATIENT SUPPORT ASSEMBLIES WITH PRECISE POSITIONING

BACKGROUND OF THE INVENTION

The field of the disclosure relates generally to systems of medical imaging, and more particularly, to magnetic resonance (MR) systems having ultra-wide bores.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

Interventional procedures use medical imaging to guide surgery procedures, improving treatment efficacy and diagnostic accuracy. Interventional procedures, however, are typical not performed with MR systems, instead with ultrasound systems. Known methods are disadvantaged in some aspects and improvements are desired.

SUMMARY OF THE INVENTION

In one aspect, a magnetic resonance (MR) system is provided. The MR system includes a magnet assembly defining a bore, wherein the bore has a diameter of 80 centimeter (cm) or greater, and a patient support assembly. The patient support assembly includes a table configured to accommodate a subject and configured to be positioned at least partially in the bore, and a carriage assembly attachable to the table and configured to drive the table to move in at least two degrees-of-freedom.

In another aspect, a patient support assembly of an MR system defining a bore having a diameter of 80 centimeter or greater is provided. The patient support assembly includes a table configured to accommodate a subject and configured to be positioned at least partially in the bore, and a carriage assembly attachable to the table and configured to drive the table to move in at least two degrees-of-freedom.

BRIEF DESCRIPTION OF DRAWINGS

FIG. 2A is a schematic diagram of a table in the MR system shown in FIG. 1 being moved in the z-direction.

FIG. 2B is a schematic diagram of a table in the system shown in FIG. 1 being moved in the y-direction.

FIG. 2C is a schematic diagram of a table in the system shown in FIG. 1 being moved in the x-direction.

FIG. 2D is a schematic diagram of a table in the system shown in FIG. 1 being rotated.

DETAILED DESCRIPTION

The disclosure includes magnetic resonance (MR) systems having ultra-wide bores and patient support assemblies in the MR systems with precise positioning. The systems and assemblies described herein provide flexible positioning of a subject and precise positioning of anatomies-of-interest in a magnet of the MR system. Such positioning, although standard in clinical, non-MR settings, has not been used in conventional MR imaging (MRI). The disclosure describes modifications that enable such positioning to be possible with MRI. With the flexibility and precision, interventional procedures become feasible with MR systems. As used herein, a subject is a human, an animal, or a phantom, or part of a human, an animal, or a phantom, such as an organ or tissue. An MR system is described herein as an example for illustration purposes only. Systems and assemblies described herein may be applied to other image modalities such as PET-MR (positron emission tomography-magnetic resonance) systems. Method aspects will be in part apparent and in part explicitly discussed in the following description.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as $B_0$ and extends in the longitudinal or z direction. In acquiring an MRI image, a magnetic field (referred to as an excitation field $B_1$), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal $B_1$ is terminated. To use the MR signals to generate an image of a subject, magnetic field gradient pulses ($G_x$, $G_y$, and $G_z$) are used. The gradient pulses are used to scan through the k-space, the space of spatial frequencies or inverse of distances. A Fourier relationship exists between the acquired MR signals and an image of the subject, and therefore the image of the subject may be derived by Fourier transform of the MR signals.

Figure 1:
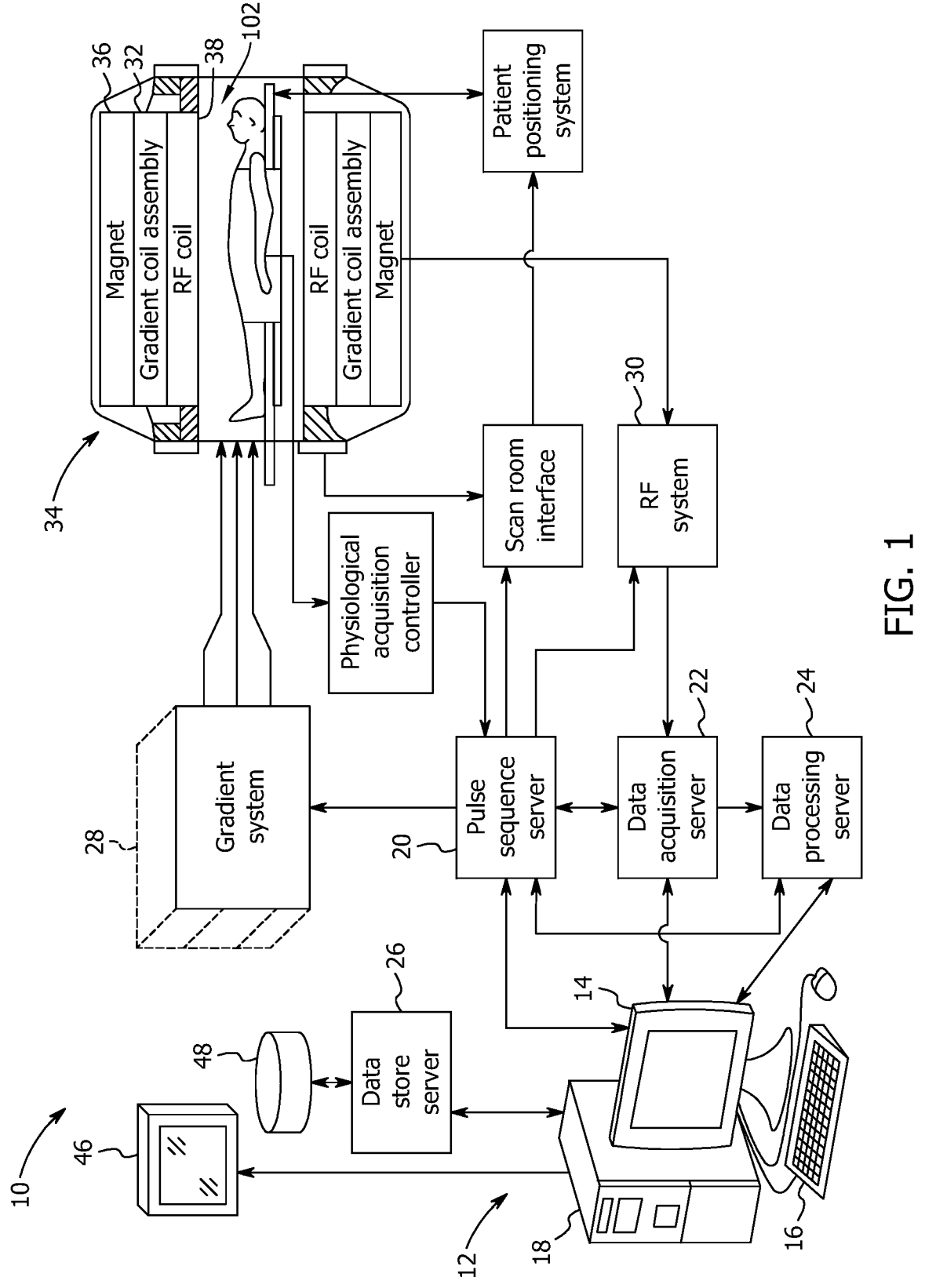
FIG. 1 is a schematic diagram of an example magnetic resonance (MR) system.

FIG. 1 illustrates a schematic diagram of an example MR system 10. In the example embodiment, MR system 10 includes a workstation 12 having a display 14 and a keyboard 16. Workstation 12 includes a processor 18, such as a commercially available programmable machine running a commercially available operating system. Workstation 12 provides an operator interface that allows scan prescriptions to be entered into MR system 10. Workstation 12 is coupled to a pulse sequence server 20, a data acquisition server 22, a data processing server 24, and a data store server 26. Workstation 12 and each server 20, 22, 24, and 26 communicate with each other.

In the example embodiment, pulse sequence server 20 responds to instructions downloaded from workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. RF coil 38 is shown as a whole body RF coil. RF coil 38 may also be a local coil that may be placed in proximity to the anatomy to be imaged, or a coil array that includes a plurality of coils.

In the example embodiment, gradient waveforms used to perform the prescribed scan are produced and applied to gradient system 28, which excites gradient coils in gradient coil assembly 32 to produce the magnetic field gradients $G_x$, $G_y$, and $G_z$ used for position-encoding MR signals. Gradient coil assembly 32 forms part of a magnet assembly 34 that also includes a polarizing magnet 36 configured to generate a polarizing magnetic field $B_0$ and RF coil 38.

In the example embodiment, RF system 30 includes an RF transmitter for producing RF pulses used in MR pulse sequences. The RF transmitter is responsive to the scan prescription and direction from pulse sequence server 20 to produce RF pulses of a desired frequency, phase, and pulse amplitude waveform. The generated RF pulses may be applied to RF coil 38 by RF system 30. Responsive MR signals detected by RF coil 38 are received by RF system 30, amplified, demodulated, filtered, and digitized under direction of commands produced by pulse sequence server 20. RF coil 38 is described as a transmit and receive coil such that RF coil 38 transmits RF pulses and detects MR signals. In one embodiment, MR system 10 may include a transmit RF coil that transmits RF pulses and a separate receive coil that detects MR signals. A transmission channel of RF system 30 may be connected to a RF transmission coil and a receiver channel may be connected to a separate RF receive coil. Often, the transmission channel is connected to the whole body RF coil 38 and each receiver section is connected to a separate local RF coil.

In the example embodiment, RF system 30 also includes one or more RF receiver channels. Each RF receiver channel includes an RF amplifier that amplifies the MR signal received by RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2}\,;\qquad(1)$$

and the phase of the received MR signal may also be determined as in Eq. (2) below:

$$\varphi = \tan^{-1}\!\left(\frac{Q}{I}\right).\qquad(2)$$

In the example embodiment, the digitized MR signal samples produced by RF system 30 are received by data acquisition server 22. Data acquisition server 22 may operate in response to instructions downloaded from workstation 12 to receive real-time MR data and provide buffer storage such that no data is lost by data overrun. In some scans, data acquisition server 22 does little more than pass the acquired MR data to data processing server 24. In scans that need information derived from acquired MR data to control further performance of the scan, however, data acquisition server 22 is programmed to produce the needed information and convey it to pulse sequence server 20. For example, during prescans, MR data is acquired and used to calibrate the pulse sequence performed by pulse sequence server 20. Also, navigator signals may be acquired during a scan and used to adjust the operating parameters of RF system 30 or gradient system 28, or to control the view order in which k-space is sampled.

In the example embodiment, data processing server 24 receives MR data from data acquisition server 22 and processes it in accordance with instructions downloaded from workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the example embodiment, images reconstructed by data processing server 24 are conveyed back to, and stored at, workstation 12. In some embodiments, real-time images are stored in a database memory cache (not shown in FIG. 1), from which they may be output to operator display 14 or a display 46 that is located near magnet assembly 34 for use by attending physicians. Batch mode images or selected real time images may be stored in a host database on disc storage 48 or on a cloud. When such images have been reconstructed and transferred to storage, data processing server 24 notifies data store server 26. Workstation 12 may be used by an operator to archive the images, produce films, or send the images via a network to other facilities.

Magnet assembly 34 defines a bore 102 sized to receive a subject. Magnet assembly 34 may be referred to as a closed bore system, where bore 102 is cylindrical (also see FIG. 5B described later). In conventional magnet assemblies, the diameter of the bore in the x-y direction is approximately 60 cm (see FIG. 5A described later). At times the diameter of the bore of a conventional MR system may be 70 cm. A bore with a diameter 80 cm or greater may be referred to as an ultra-wide bore. The conventional wisdom in MR teaches against a magnet assembly having an ultra-wide bore for the following reasons. Uniform magnetic field in the bore is needed to ensure imaging quality of the system because magnetic field, changes in magnetic field via gradients, and effects of changes in the subject on magnetic fields are used in generating images and spectra of the subject and detecting functions in the subject. With the increase of a bore diameter, the difficulties in achieving field uniformity increase. The amount of energy used in driving gradient coils increases drastically in a magnet assembly having an increased bore, where the electric power required to operate a gradient coil scales with the fifth power of the radius of the bore. With the drastic increase in electric power being applied, the amount of heat generated by operation of gradient coils also increases drastically. Further, with the increase of the bore size, the magnet assembly may become too large to fit into a standard scanner room, causing increase in installation costs and labor. As a result, having an ultra-wide bore in a magnet assembly is discouraged by the costs and technical difficulties.

In conventional magnet assembly, where the bore has a typical diameter of 60 cm or 70 cm, the table has only one degree-of-freedom in movement, where the table may only be moved in and out of the bore in a superior-inferior direction or the z direction of the magnet assembly, due to the limited dimension of the bore. The limited degree-of-freedom in movement of the table in conventional magnet assembly restricts the applications that can be performed in an MRI system and causes other problems. For example, magnet uniformity and gradient linearity tends to decrease at locations away from the iso-center of the magnet. Anatomies-of-interest should be positioned in the optimum imaging regions for optimal imaging quality. A region including the isocenter and locations proximate the isocenter is referred to as an optimum imaging region. At an optimum imaging region, homogeneity of the magnetic field is high, such as variation in magnetic field being 1 ppm or less, and linearity of gradients is high, such as deviation from linearity being 17% or less. An optimum imaging region has a field-of-view of 30 cm-45 cm in the radial direction or in the x-y plane and 30 cm-40 cm in the axial direction or the z direction, which is much smaller than a bore space. With only one degree-of-freedom in movement, anatomies such as extremities would not be positioned at the isocenter or locations proximate the isocenter, causing imaging distortion and artifacts. The positioning issues are compounded by the fact that to minimize magnet size and weight, the imaging field-of-view is kept small. Increasing the imaging field-of-view comes with increasing penalties of magnet size, weight, and cost.

In conventional MR system, the subject may be requested to be in unnatural positions to place the anatomies-of-interest in the optimum imaging region. For example, to image the wrist or elbow, the current clinical standard is to have the subject be positioned in the prone position with the forearm extended such that the wrist or elbow is in the optimum imaging region, which is the so-called "superman" position. Such unnatural positions are uncomfortable for the subject to maintain for a long period of time, and may be difficult for some subject due to injuries such as shoulder injuries. An MR imaging session typical lasts several minutes. Holding at unnatural positions causes patient discomfort and motion from the subject due to the urge to adjust the position to alleviate discomfort, causing imaging distortion and artifacts from the motion. Further, due to the limited size of the bore, scanning at certain positions are not available in conventional magnet assemblies such as sitting positions. In addition, in interventional applications, surgeries, diagnosis, treatment, or therapies are performed at positions other than the only available position of being supine or prone with the whole body on the table. To perform surgeries with an MR system using MR images to guide the operation, the surgeon is forced to operate at the only available positions instead of optimal positions, resulting in errors and/or unsatisfactory or suboptimal results and reduced access to the anatomy-of-interest. As a result, interventional procedures are not feasible with conventional MR systems.

In contrast, systems and assemblies described herein provide a table having up to six degrees-of-freedom in movement in a ultra-wide bore system. The additional degrees-of-freedom in movement of the table allow positioning the anatomy-of-interest in the optimum imaging region, thereby increasing the image quality. Further, precise positioning of anatomies such as the wrist and/or elbow allows the subject to be in a comfortable supine position with the forearm at the natural position of being next to the body. No extraordinary extension is necessary, allowing imaging anatomies-of-interest at the optimum imaging region independent of subject habitus and increasing patient comfort. Systems and assemblies described herein also allows optimal surgery positions such as lithotomy positions for pelvic surgery or image-guided prostate biopsy, and accommodate a Wilson table for spinal surgery, thereby facilitating interventional procedures in an MR scanner, which are unavailable with conventional MR systems. In addition, systems and assemblies described herein accommodate imaging of the subject at new positions unavailable in conventional MR systems, such as being seated, thereby increasing applications of MR in diagnosis and treatment.

Figure 2E:
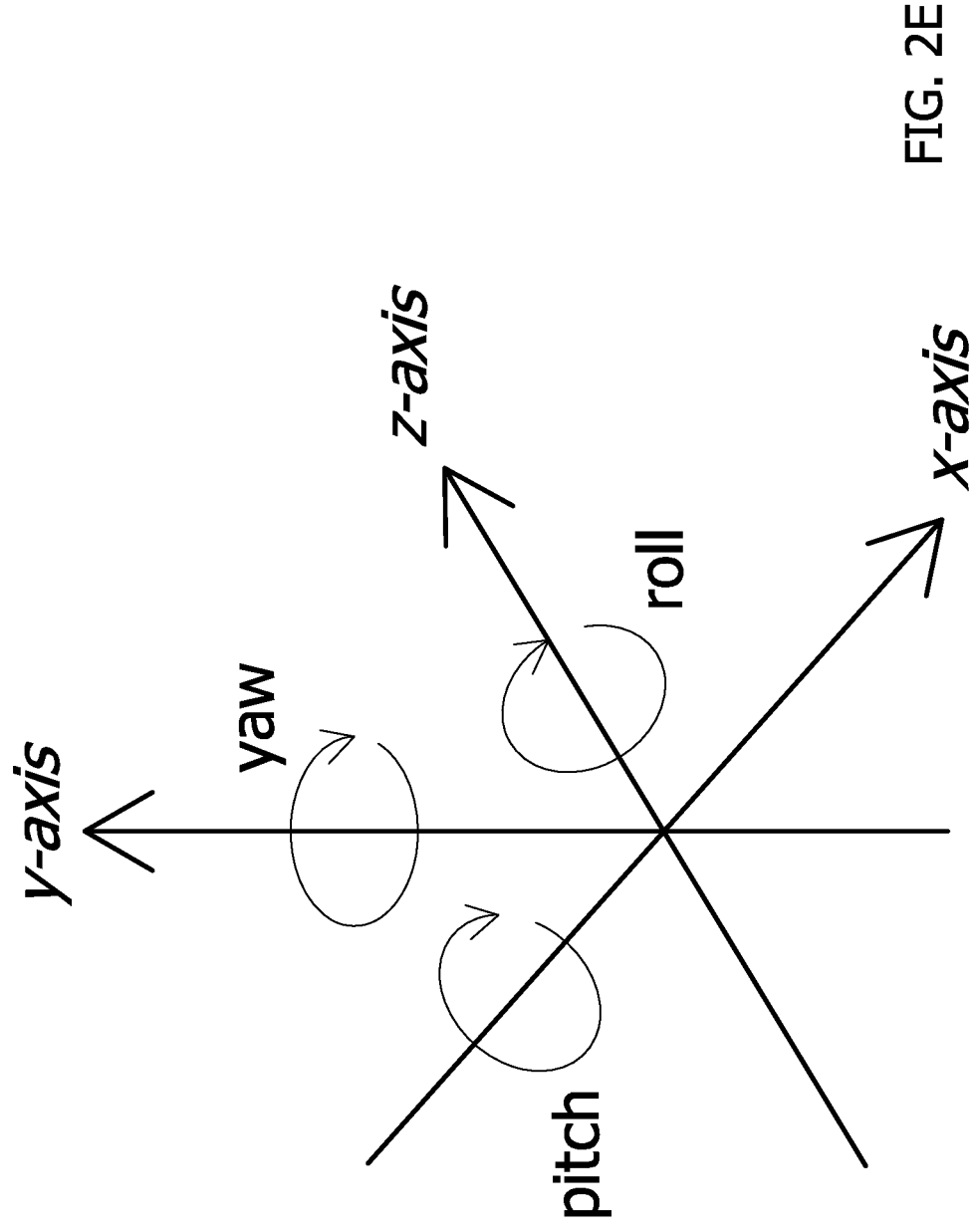
FIG. 2E shows example rotations in an MR system.

FIGS. 2A-2E shows movement provided by an example patient support assembly 200. In an MR system, the superior-inferior direction is referred to as a z-direction, which is the direction of the main magnetic field $B_0$ (see FIG. 2E). An x-y plane is a plane perpendicular to the z-axis. An x direction is along the left-and-right direction. A y direction is along the anterior-posterior direction. In the example embodiment, a table 202 may be moved along a z direction (see FIG. 2A). Table 202 may be moved vertically, or up and down, within bore 102 of magnet assembly 34. along a y direction (see FIG. 2B). Table 202 may be moved laterally left and right within bore 102 of magnet assembly 34 along an x direction (see FIG. 2C). Table 202 may be translated to any position in bore 102 of magnet assembly 34. Table 202 may be rotated along x-axis, y-axis, or z-axis, or along a line 203 in the table, such as along a line 203 that an axis has been rotated to (see FIGS. 2D and 2E). For example, as shown in FIG. 2D, after table 202 is rotated around the y axis, the z-axis has been rotated around the y axis to a line 203 at an angle with the z-axis, and table 202 is rotated around line 203. A pitch of table 202 may be adjusted to provide a Trendelenburg orientation or a reverse Trendelenburg orientation of the subject within bore 102 by rotating about the x axis. The movements may be sequential or combined into one movement such that table 202 is moved to a desired location and/or orientation. As a result, six degrees-of-freedom in movement are provided, where table 202 may be moved along a x direction, a y direction, or a z direction, rotated around an x-axis, a y axis, or z axis, or any combination thereof. To move table 202, table 202 may be driven by a motor and moved or rotated. Other mechanisms or forces may be used to drive the movement of table 202 such as a pneumatic mechanism or a hydraulic mechanism.

Figures 3A, 3B:
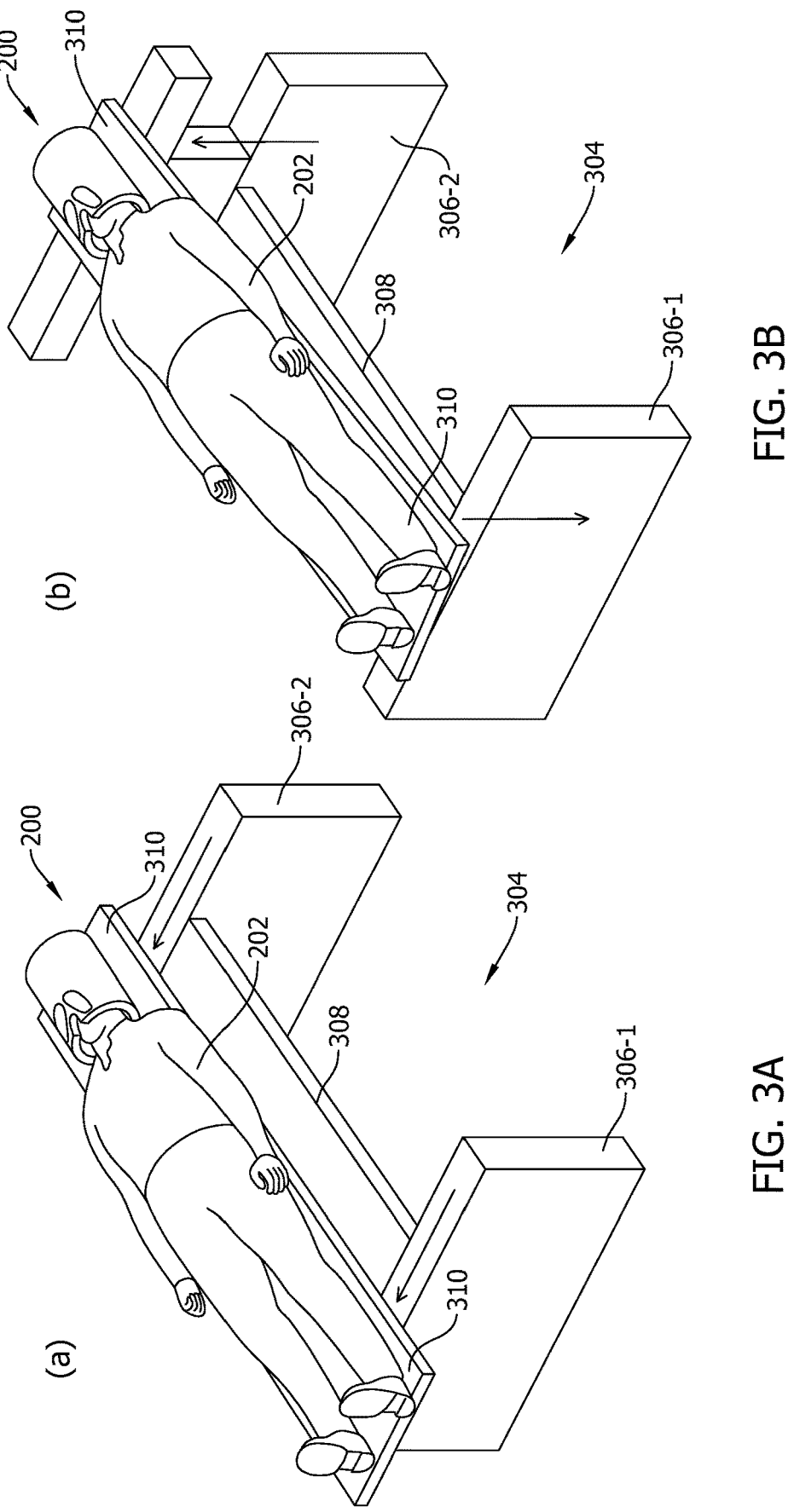
FIG. 3A is a schematic diagram of an example embodiment of a patient support assembly in the MR system shown in FIG. 1.
FIG. 3B is a schematic diagram of another example embodiment of a patient support assembly in the MR system shown in FIG. 1.
Figure 3C:
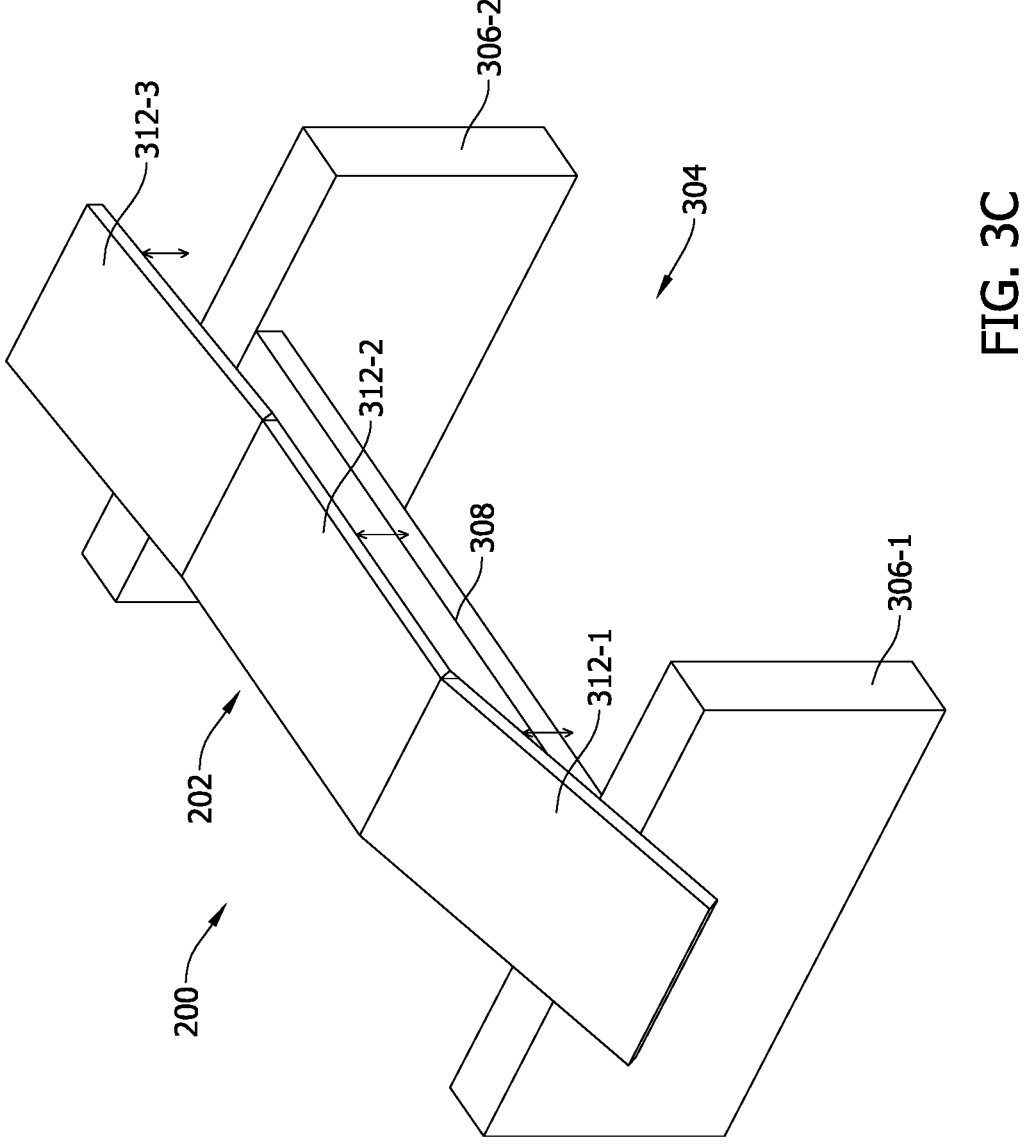
FIG. 3C is a schematic diagram of one more example embodiment of a patient support assembly in the MR system shown in FIG. 1.

FIGS. 3A-3B show example embodiments of patient support assemblies 200. In the example embodiments, table 202 may be moved along the x direction (FIG. 3A). Moving in the x direction is not needed in non-MR setting because a surgeon may simply walk close or away or move the optional operation robot close or away from the subject. Table 202 may be tilted (FIG. 3B) within bore 102. Parts of table 202 may be moved independently (FIGS. 3A-3C). Patient support assembly 200 includes table 202 and a carriage assembly 304. Carriage assembly 304 is attachable to table 202 and configured to drive table 202 to move in two or more degrees-of-freedom. Carriage assembly 304 may include a front table support 306-1 and a rear table support 306-2. Table supports 306 are connected with one another via a bridge 308. Table supports 306 and bridge 308 form a platform to place table 202 thereon. One or both table supports 306 may be positioned inside an enclosure 502 that encloses magnet assembly 34 (see FIG. 5B). Alternatively, one or both table supports 306 are positioned outside enclosure 502. Table supports 306 are positioned proximate to ends 503 of magnet assembly 34. Individual table supports 306 may be moved independently from one another to enable a plethora of patient positioning variations to meet the clinical needs of clinical procedures.

In the example embodiments, ends 310 of table 202 may be independently driven from one another (FIG. 3B). For example, front table support 306-1 may be independently controlled and move in the y direction from rear table support 306-2. Table supports 306 may be independently controlled to effect a reverse Tredelenburg position for intraoperative surgical procedure in the brain or a tilted lithotomy position or a Trendelenburg position for pelvic or lower abdominal surgery such as image-guide prostate biopsy. In some circumstances, a subject is unable to tolerate a supine position in a scanner, for example, due to fluid built-up in the lungs. Positioning the subject in the reverse Trendelenburg position are advantageous in avoiding exacerbation of the condition, providing improved patient comfort and minimizing motion during MR scans due to discomfort. Table supports 306 may be independently controlled such that ends 310 of table 202 move independently in the x direction to effect a rotation around the y axis. Table 202 may be driven to move along other directions such as the z direction and/or the y direction and rotate around the x, y, and/or z axes.

In some embodiments, sections of table 202 may be moved independently and relative to one another such that the different sections of the subject is at different heights (FIG. 3C). Table 202 may include a first section 312-1, a second section 312-2, and a third section 312-3. Table 202 may be articulated at the joints between different sections 312. Other number of independently movable sections may be included in table 202, such as two or four. When a subject is positioned on table 202, the heights of sections 312 may be individually adjusted such that the head, the trunk, and the leg may be at different heights. For spine or abdominal surgery, it is desirable that different sections of the subject are at different positions, such as abdomen being elevated relative to the head or feet. Articulated table 202 and individually-controllable sections 312 provide customized elevation or depression of various sections of the subject.

Systems and assemblies described herein are advantageous in providing precise positioning of the anatomy-of-interest in the optimum imaging region, thereby improving image quality and increase diagnostic accuracy. For example, in breast imaging, the anatomy of interest such as the breast and the axilla is outside the optimum imaging region. As such, for procedures such as diffusion imaging, correction of gradient non-linearity is needed, which requires additional hardware and/or software. Further, magnetic field inhomogeneities may be different between the left and right breast regions when neither of the regions is in the optimum imaging regions, requiring additional processes and compensation. In one more example, systems and assemblies provide precise positioning of anatomies-of-interest in the optimum imaging region for different subjects, unlike in conventional MR systems, where due to the limited space in the bore and limited movement of the table, anatomies-of-interest could not be positioned in the optimum imaging region for some subjects.

Due to the limited space and inflexible positioning of the subject in conventional MR systems, interventional procedures are typically not performed with MR systems, instead with ultrasound imaging. Interventional procedures are procedures guided by images, and may be referred to as intraoperative procedures or interventional and intraoperative procedures. The image quality of ultrasound imaging, however, is far inferior to MR. In known systems, MR-ultrasound fusion methods are used, which has drawbacks and difficulties of conventional MR systems and low imaging quality of ultrasound images in addition to the difficulties in fusing MR images with ultrasound images.

In contrast, systems and assemblies described herein are advantageous in providing ranges and flexibility of movement of the table, thereby facilitating interventional procedures such as image guided biopsy for breast, prostate, and liver, intraoperative image-guided surgery for brain, head, and neck lesions such as non-Hodgkin's lymphoma. Systems and assemblies described herein are advantageous in providing any positioning of the subject suitable for an interventional procedure such that the subject is comfortable, the surgeon has optimal access to the anatomies-of-interest, and the images of the anatomies-of-interest are optimal for surgery and examination. For example, in neurosurgery, a subject should be in a reverse Trendelenburg position such that brain and blood remain with the subject during the surgery to reduce complication or difficulties in surgery. In another example, MR is used to ensure margins of tumor is fully resected in interventional procedures, taking advantage of the superior soft tissue contrast achieved by MR, compared to ultrasound imaging. Systems and assemblies described herein are also advantageous over conventional operation tables in providing any operation position of the subject in one single system.

Figure 4:
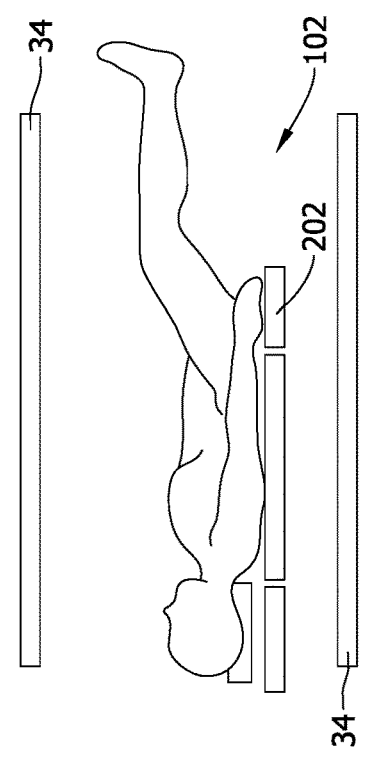
FIG. 4 shows lithotomy positions accommodated by the MR system shown in FIG. 1.
Figure 4:
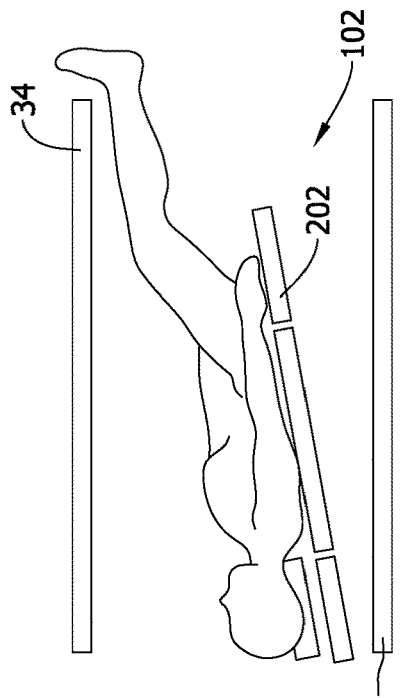
Figure 4:
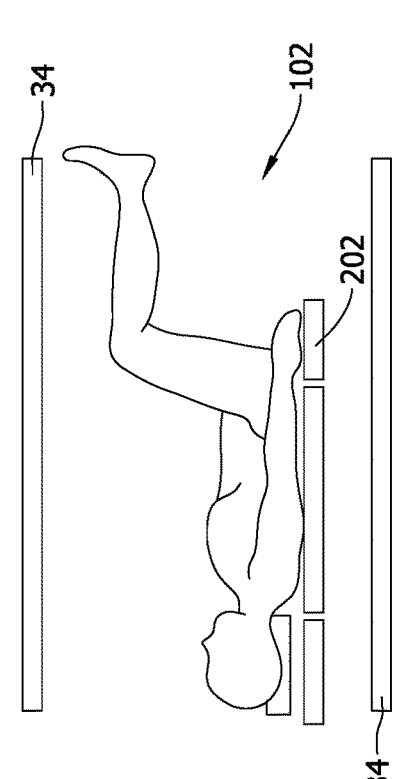
Figure 4:
Figure 4:
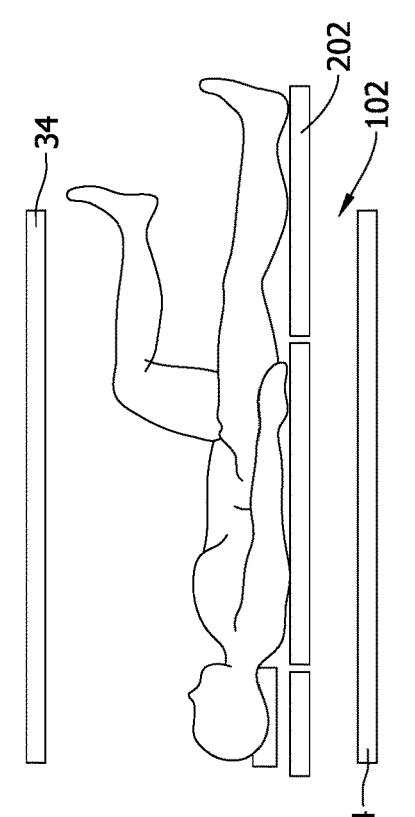

FIG. 4 shows lithotomy positions are provided with systems and assemblies described herein. Lithotomy positions are suitable for pelvic and lower abdominal surgery. In the example embodiment, table 202 may be tilted. Ultrawide bore 102 also provides space to move the leg of the subject to be at various heights, even after table 202 has been tilted. A cushion or a stirrup may be provided to facilitate different leg heights. Lithotomy positions are unavailable in conventional magnet assemblies due to the limited bore size and the restricted movement of the table of being along the z-direction only. Various lithotomy positions also allow flexion/extension musculoskeletal studies. Hip motions are studied by active imaging as the subject moves from a supine position to a hemi or split lithotomy position. In addition, active flexion extension may be studied under load or flexion for examining defects or injuries in joints, such as the elbow, the knee, or the hip. Such changes in position or various positions are unavailable in conventional MR systems either.

Figure 5A:
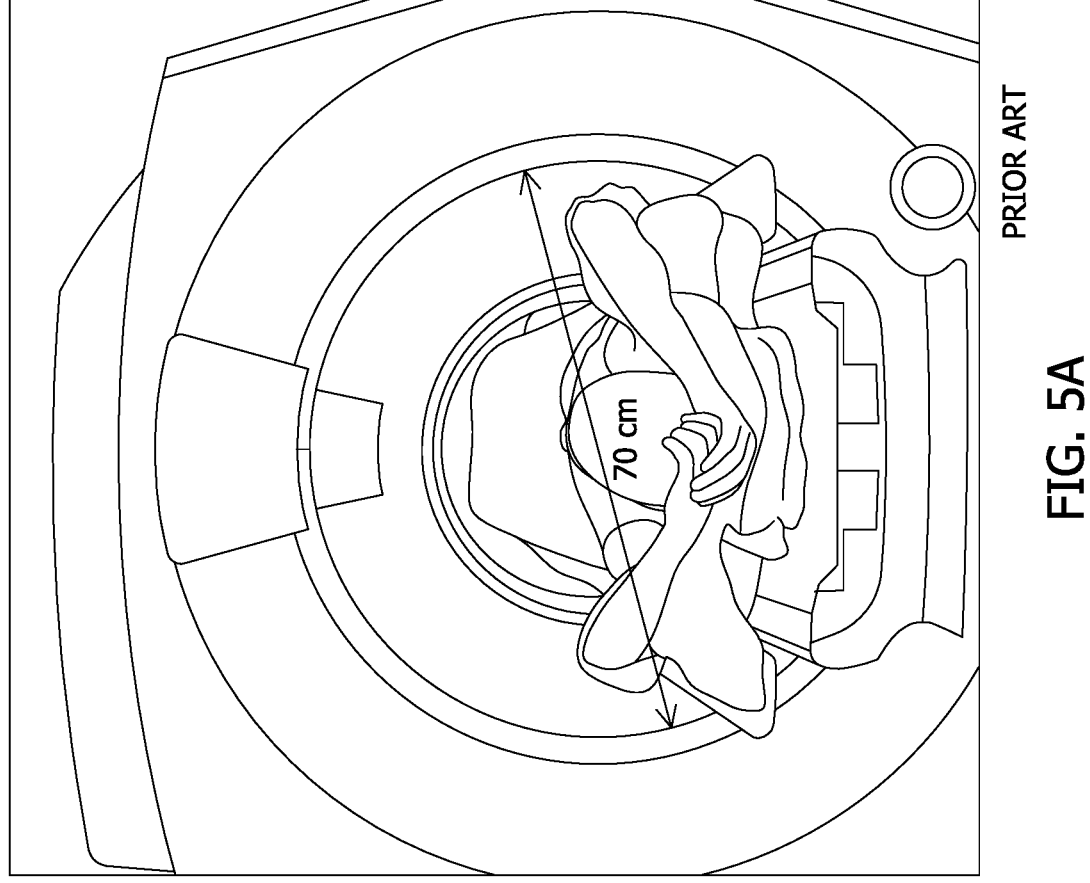
FIG. 5A shows a conventional MR system.
Figures 5B, 5C:
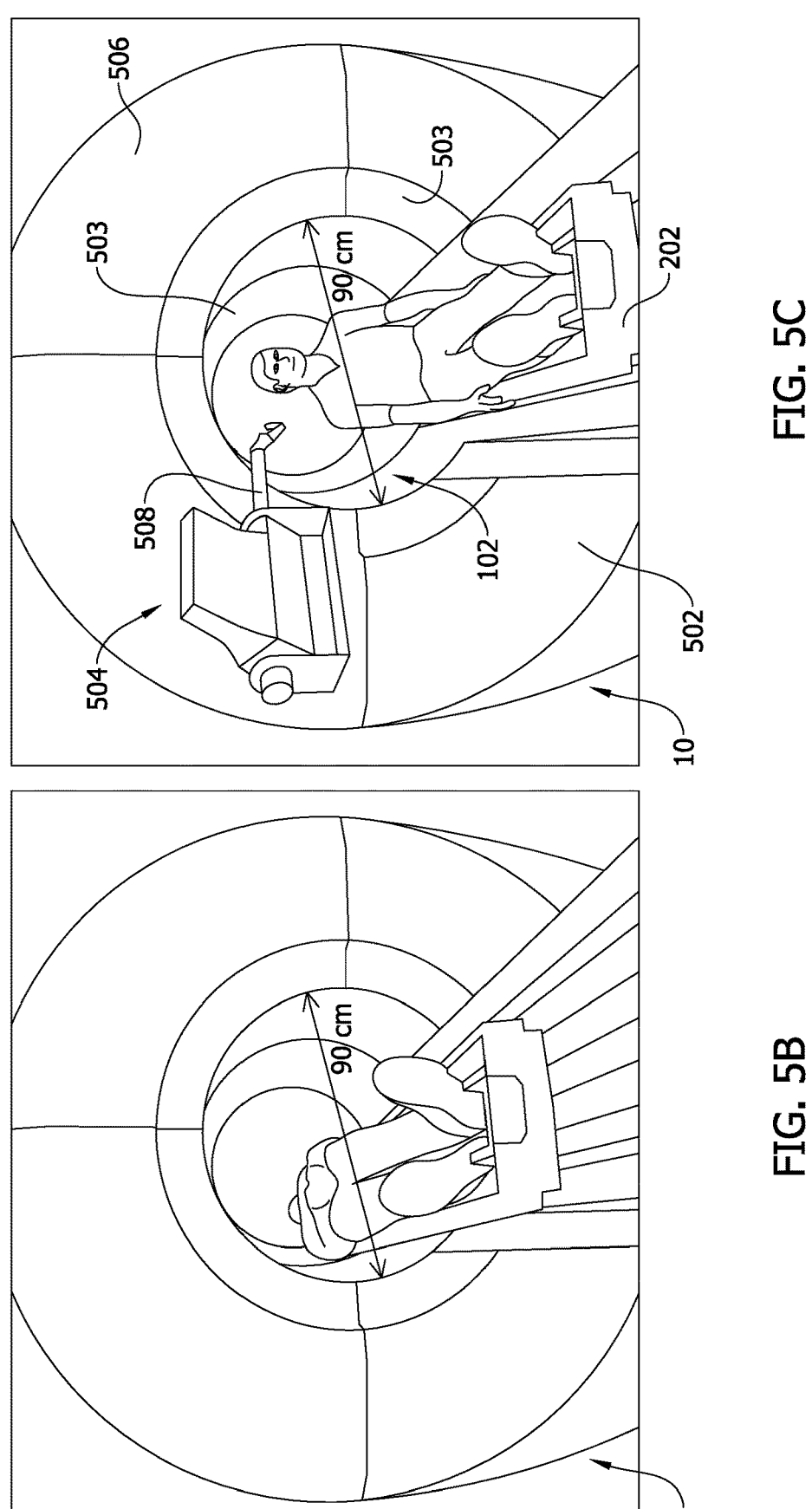
FIG. 5B shows an example MR system with an ultra-wide bore with a subject lying on a table, showing the table elevated and shifted to one side to have the left hip at the isocenter of the magnet.
FIG. 5C illustrates the MR system shown in FIG. 5B with the subject in a sitting position.

FIGS. 5A-5C show an ultra-wide bore 102 allows imaging a subject while in a sitting position. FIG. 5A shows a conventional magnet assembly, where the bore has a diameter of 70 cm, leaving little extra space in the bore besides the subject. FIGS. 5B and 5C show an example ultra-wide bore 102. In the example embodiment, bore 102 has a diameter of 90 cm. In FIG. 5B, the extra space allows for the subject to be positioned such that the left hip is at the magnet isocenter, where the patient table is raised and shifted to one side. A subject may also be seated during scanning (see FIG. 5C). Imaging while seated is advantageous because at this position, a modest load is placed on lumbar or thoracic spine and the organs in the abdomen are at natural positions, similar to standing, thereby increasing the subject comfort and imaging and diagnostic accuracy by imaging the anatomies-of-interest under modest load and/or at natural positions.

Further, systems and assemblies described herein allow access of robotic devices in image-guided interventional procedures. Robotic devices are advantageous over surgeons in minimizing tremor or vibration and increasing operation precision. In systems and assemblies described herein, a robot assembly 504 may be positioned on an exterior face 506 of magnet assembly 34. Alternatively, robot assembly 504 may be placed on carriage assembly 304 or on table 202, mounted on other part of magnet assembly 34, or placed on the floor proximate the subject. An articulated arm 508 of robot assembly 504 may be extended into bore 102 to operate on the subject. In contrast, in conventional MR systems, robotic devices typically require complicated arm design for the arm to be fitted into the bore because of the limited available space in the bore after the subject has been positioned inside (such as that shown in FIG. 5A), and often using robotic devices is infeasible due to the lack of space. Additionally, although robotic devices may be modified to use the limited available space of conventional MRI scanners, this sacrifices the precision and control of surgical robots. As such, robotic-assisted surgery/intervention is infeasible or impractical in conventional MRI scanners.

Accordingly, systems and assemblies described herein provide MR-guided interventional procedures, which is currently unavailable or is not attractive to surgeons due to limited gain and added discomfort and/or difficulties.

At least one technical effect of the systems and assemblies described herein includes (a) an interventional MR system; (b) a table moveable in at least two degrees-of-freedom; (c) precise positioning of anatomies-of-interest to the optimum imaging region; and (d) new imaging positions unavailable with conventional MR system.

Example embodiments of MR systems and patient support assemblies are described above in detail. The systems and assemblies are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A magnetic resonance (MR) system, comprising:
a magnet assembly comprising a superconducting magnet, the magnet assembly being a closed bore system and defining a bore, wherein the bore has a diameter of 80 centimeter (cm) or greater and a length equal to or greater than 1 meter, the magnet assembly defining an imaging region in the bore having a variation in magnetic field being 1 ppm or less and deviation from linearity of gradients being 17% or less, the imaging region having a field of view being at least one of i) greater than 45 cm in an x-y plane of the MR system or ii) greater than 40 cm in a z direction of the MR system; and
a patient support assembly comprising:
a table configured to accommodate a subject and configured to be positioned at least partially in the bore, the table configured to position the subject at least partially in the bore; and a carriage assembly attachable to the table and configured to drive the table to move in six degrees-of-freedom while the table is at least partially in the bore to position an anatomy-of-interest of the subject in the imaging region in the bore, the six degrees-of-freedom including moving along an x direction, a y direction, or the z direction of the MR system and rotating around an x-axis, a y axis, or a z axis of the MR system.

2. The MR system of claim 1, wherein the carriage assembly is configured to drive the table to position the subject at a position that facilitates an interventional procedure.

3. The MR system of claim 1, wherein the carriage assembly is configured to drive the table to move in a left-and-right direction.

4. The MR system of claim 1, wherein the carriage assembly is configured to drive the table to move in an anterior-posterior direction.

5. The MR system of claim 1, wherein the table comprises a first end and a second end opposite the first end in a superior-inferior direction, wherein the patient support assembly is configured to drive the first end and the second end independently while the table is at least partially in the bore.

6. The MR system of claim 1, wherein the table comprises a first section, a second section, and a third section articulated with one another, and the carriage assembly is configured to drive the first section, the second section, and the third section independently while the table is at least partially in the bore.

7. The MR system of claim 1, wherein the carriage assembly is configured to drive the table to rotate.

8. The MR system of claim 1, wherein the carriage assembly is configured to position the table in a Trendelenburg orientation or a reverse Trendelenburg orientation.

9. The MR system of claim 1, wherein the MR system is configured to accommodate the subject in a lithotomy position.

10. The MR system of claim 1, wherein the bore is sized to accommodate the subject in a sitting position, and the MR system further comprises a robot assembly coupled to the magnet assembly and configured to operate on the subject.

11. The MR system of claim 10, wherein the robot assembly is positioned on an exterior face of the magnet assembly, the robot assembly further comprising an articulated arm configured to extend into the bore.

12. A patient support assembly of a magnetic resonance (MR) system including a magnet assembly, the magnet assembly including a superconducting magnet and being a closed bore system, the magnet assembly defining a bore having a diameter of 80 centimeter or greater and a length equal to or greater than 1 meter, the magnet assembly defining an imaging region in the bore having a variation in magnetic field being 1 ppm or less and deviation from linearity of gradients being 17% or less, the imaging region having a field of view being at least one of i) greater than 45 cm in an x-y plane of the MR system or ii) greater than 40 cm in a z direction of the MR system, the patient support assembly comprising:
a table configured to accommodate a subject and configured to be positioned at least partially in the bore, the table configured to position the subject at least partially in the bore; and
a carriage assembly attachable to the table and configured to drive the table to move in six degrees-of-freedom while the table is at least partially in the bore to position an anatomy-of-interest of the subject in the imaging region in the bore, the six degrees-of-freedom including moving along an x direction, a y direction, or the z direction of the MR system and rotating around an x-axis, a y axis, or a z axis of the MR system.

13. The patient support assembly of claim 12, wherein the carriage assembly further comprises:

a front table support coupled with a first end of the table and configured to control the first end; and a rear table support coupled with a second end of the table opposite the first end and configured to control the second end, wherein the front table support and the rear table support are configured to control the first end and the second end independently while the table is at least partially in the bore.

14. The patient support assembly of claim 12, wherein the table comprises a first section, a second section, and a third section articulated with one another, and the carriage assembly is configured to drive the first section, the second section, and the third section independently while the table is at least partially in the bore.

15. The patient support assembly of claim 12, wherein the carriage assembly is configured to position the table in a Trendelenburg orientation or a reverse Trendelenburg orientation.

16. The patient support assembly of claim 12, wherein the carriage assembly is configured to drive the table to move in a left-and-right direction and/or an anterior-posterior direction.

17. The patient support assembly of claim 12, wherein the carriage assembly is configured to drive the table to rotate.

* * * * *